United States Patent
Ly

(10) Patent No.: US 6,517,521 B1
(45) Date of Patent: Feb. 11, 2003

(54) PAINLESS PERFORATED INTRADERMAL INJECTION NEEDLE

(75) Inventor: Keith K. Ly, 2312 N. 134th St., Apt. #1, Seattle, WA (US) 98133

(73) Assignee: Keith K. Ly, Seattle, WA (US)

(*) Notice: Subject to any disclaimer, the term of this patent is extended or adjusted under 35 U.S.C. 154(b) by 0 days.

(21) Appl. No.: 09/552,200

(22) Filed: Apr. 19, 2000

Related U.S. Application Data

(60) Provisional application No. 60/130,469, filed on Apr. 22, 1999.

(51) Int. Cl.$^7$ .................................................. A61M 5/31
(52) U.S. Cl. ........................................ 604/239; 604/272
(58) Field of Search ................................ 604/239, 272, 604/274, 506, 411, 170.03, 167.05

(56) References Cited

U.S. PATENT DOCUMENTS

| 648,858 A | 5/1900 | Dolge | |
|---|---|---|---|
| 4,002,174 A | 1/1977 | Reed et al. | |
| 4,411,657 A | * 10/1983 | Galindo | 604/274 |
| 4,710,180 A | * 12/1987 | Johnson | 604/239 |
| 5,254,106 A | 10/1993 | Feaster | |

FOREIGN PATENT DOCUMENTS

| EP | 704160 | 5/1996 |
|---|---|---|
| EP | 761173 | 4/1997 |

OTHER PUBLICATIONS

Fletcher, G. C. et al., "The effect of temperature upon pain during injection of propofol," Anesthesia, 1996, May, 51(5), pp. 489–9 (abstract).

Parham, S. M, et al., "Effect of pH modification by bicarbonate on pain after subcutaneous injection," Can. J. Surgery, 1996, Feb., 39(1) pp. 31–35 (abstract).

Palmon, S. C. et al., "The effect of needle gauge and lidocaine pH on pain during intradermal injection" Anesth. Analg. 1998, Feb., 86(2), pp. 379–381.

Jorgensen, J. T. et al. "Pain assessment of subcutaneous injections," Ann. Pharmacotherapy, 1996, Jul.–Aug., 30(7–8), pp. 729–732 (abstract).

Simone et al, "Dose–dependent pain and mechanical hyperalgesia in humans after intradermal injection of capsaicin," Pain 38(1989), pp. 99–107.

Bonica, J.J. The Management of Pain. Philadelphia, Lea & Febiger, 1990, vol. I, pp. 597–625 and vol. II, pp. 592–605.

* cited by examiner

Primary Examiner—Teresa Walberg
Assistant Examiner—Vinod D. Patel
(74) Attorney, Agent, or Firm—Robert M. Hunter

(57) ABSTRACT

An improved hypodermic needle that greatly reduces the pain associated with injection through the skin that includes a translucent hub for quick observation of flashback, a regular-wall needle with multiple strategically-placed lateral perforations ending with a blade-like honed edge orifice which the remainder of the injection fluid escapes. The increase in localized surface area through which fluid leaves the needle decreases the mechanical distortion of the surrounding tissue thereby lessening pain receptor stimulation and reducing the perception of pain during the injection process.

20 Claims, 2 Drawing Sheets

PAINLESS PERFORATED INTRADERMAL INJECTION NEEDLE

CROSS-REFERENCE TO RELATED APPLICATIONS

This application claims the benefit of U.S. Provisional Application No. 60/130,469, filed Apr. 22, 1999.

STATEMENT REGARDING FEDERALLY SPONSORED RESEARCH OR DEVELOPMENT

Not Applicable

BACKGROUND OF THE INVENTION

This invention relates generally to a hypodermic needle that is useful for applying a local anesthetic to block nerve transmission, otherwise known as regional anesthesia or any intramuscular injection of medications requiring skin penetration.

The somatic senses are the nervous system mechanisms that collect sensory information throughout the body. They are classified into three different physiological types: (1) the mechanoreceptive somatic senses, stimulated by the mechanical displacement of some tissue of the body, (2) the thermoreceptive senses, which detect heat and cold, and (3) the chemoreceptive senses, which are activated by excess hydrogen ion (i.e., an acidic environment). There are at least six different types of tactile receptors known, but many more similar ones also exist. Some examples are free nerve endings, which are found everywhere in the skin and many other tissues; Meissners corpuscles, encapsulated nerve endings that excite a large (type AB) myelinated sensory nerve fiber; Merkels discs and Iggo dome receptors which project upward against the underside of the epithelium of the skin; Pacimian corpuscles which are deeper in the skin tissue of the body for detecting vibration or other changes in mechanical positioning. When activated, these receptors send neurochemical signals to the brain to be processed and acted upon in response to a stimulus.

Pain is a protective mechanism for the body. It occurs whenever any tissues are being damaged, and it causes the individual to react by moving away from the pain stimulus. The pain receptors in the skin and other tissues are mainly free nerve endings. They are widespread in superficial layers of the skin and also in certain internal tissues, such as the periosteum, the arterial walls, the joint surfaces, and the falx and tentorium of the cranial vault. Most of the other deep tissues are not extensively supplied with pain endings but are sparsely supplied, but, nevertheless, any widespread tissue damage can still summate to cause an aching type of pain in these areas. Therefore, anything that is deposited under the dermal layer causing distension will be sensed by receptors and will be activated according to its specificity.

There are many factors that can elicit injection pain such as temperature of the injected solution, the acidity of the solution, and the mechanical method of injecting, such as the speed and the local delivery of the fluid to a specified location, causing distension. These challenges to painless injection have been studied and many new methods of injection have been devised to lessen injection pain. For example, the temperature of the solution challenge can be overcome by warming the injected solution to 37 degrees Celsius, which will substantially reduce pain as described by Fletcher, G. C. et al., in "The effect of temperature upon pain during injection of propofol," Anesthesia, May 1996, 51(5) :489–9. The acidic nature of the injected solution often needed for storage can cause significant post injection pain. For example, lidocaine is often used for skin anesthesia and causes severe sharp pain post-injection in the dermal wound due to its high acidity. One solution is to increase the pH of the lidocaine by diluting the lidocaine with sodium bicarbonate, a base solution, which will decrease the hydrogen ion concentration to a normal body pH, thus decreasing the amount of acid (H+) ions irritating the chemoreptors. This was extensively explained in research papers by Parham, S. M. et al., entitled "Effect of pH modification by bicarbonate on pain after subcutaneous injection," Can. J. Surgery, Febauary 1996, 39(1):31–5 and Palmon, S. C. et al., entitled "The effect of needle gauge and lidocaine pH on pain during intradermal injection" Anesth. Analg. February 1998, 86(2):379–81. Both papers pointed out the significant decrease in pain associated with the intradermal injection of lidocaine mixed with bicarbonate. Also, in the last paper, Palmon et al. also demonstrated that changing needle size from 25 G to 30 G did not affect the injection pain by any significant amount.

The factor of mechanical tissue distension in the area surrounding an injection site stimulating mechanosensitive pain receptors has been well studied but has not yet been challenged. When activated, these receptors transduce pain via the fast mechanico C-pain fibers that induce a severe pain sensation. The pain sensations caused by tissue distension tell the body of impending injury. This effect was observed by Jorgensen, J. T. et al. and reported in "Pain assessment of subcutaneous injections," Ann. Pharmacotherapy, July–August 1996, 30(7–8): 729–32 1996, and by Simone et al., and reported in "Dose-dependent pain and mechanical hyperalgesia in humans after intradermal injection of capsaicin," Pain 38(1989), 99–107 where it was observed that even a minimal injection change from 0.5 mL to 1.0 mL will significantly increase local pain in the injected area from distension. Also, these papers demonstrated that the distention resulted in additional mechanical hyperalgesia in the surrounding tissue that can last longer than twentyfour hours.

A modified conventional hypodermic needle, having a blade-like cutting edge tip for penetration of the flesh and lateral orifices through which anesthetic or other solution is ejected, can reduce pain. It has been theorized that during the process of injection, the painful stimulus that is felt by the patient during the injection is mechanical distension pain more so than pain associated with the action of the sharp needle piercing the skin. The actual tissue distension causes an activation of small delta type A fibers and mechanico C-pain receptors in the dermal and subcuticular layer throughout the body. The injected fluid displaces the nerve-ending fibers and thus causes activation of painful stimuli. The injected fluid causes local distension and therefore excites the mechano-sensitive pain receptors by causing mechanical stress or mechanical tissue damage. The mechanosensitive pain receptors are activated when mechanical stress or damage to the tissues is taking place. This was demonstrated in a study by Jorgensen, J. T. et al. in Demark which showed that there is a direct relationship between the pain of injection and the injection volume and that an increase of volume from 0.5 to 1.0 mL increases pain significantly.

The needle of the present invention, with its multi-perforated lateral holes, decreases local tissue distention and reduces the activation of many nearby skin receptors, thus decreasing mechanical pain secondary to distension during and immediately after injection of fluids. By reducing the amount of pressure that is exerted on a certain distinctive area of skin by increasing the surface area of fluid diffusion, pain can theoretically be decreased. The needle has multiple perforated distal holes all located at the distal third of the needle length which allows it to evenly dispense the injected substance over a greater area while still remaining localized to a certain tissue depth. By decreasing the pressure via increasing the outflow area, there is less local distension and, therefore, a decrease in the number of nerve endings activated/stimulated. This phenomenon is described by Bernoulli's principle that dictates the relationship between area and pressure. When an area is increased, the pressure decreases in accordance with the proportionality of the amount of fluid injected. Therefore, the patient in theory perceives less pain other variables being unchanged.

BRIEF SUMMARY OF THE INVENTION

The hypodermic injection needle of the present invention has an elongated rigid shaft of a predetermined length which varies from 0.5 to 1.5 inches and a diameter which varies from 16 G to 28 G. The shaft includes a hollow, interior passage that terminates at the tip of the needle with precise honed-edge bevel design that easily penetrates tissue with an incision that minimizes trauma. One end of the needle is fastenable to a conventional syringe. Adjacent to the needle tip, multiple lateral perforated openings along the circumference of the shaft, which are about 0.02 inch in diameter, are spaced strategically such that the injection fluid can be dispensed at approximately a 90-degree angle to the longitudinal axis of the needle shaft.

The multiple perforated openings are such that the needle disperses the injected fluid over a larger area through the lateral facing elliptical orifices (relative to the needle shaft), greatly reducing the liquid pressure on the surrounding environment, therefore creating a decrease in displacement and a decrease in activation of pain receptors.

In the preferred embodiment, the improved needle has a sharply-honed tip opening followed by a plurality of elliptical orifices (0.2 inches wide) at a variable distance of no more than thirty percent of the total needle cannula. The orifice closest to the tip is placed immediately and longitudinally adjacent to the distal opening. Four orifices for achieving multiple openings in each needle may be located at 0.0313 inch intervals staggered around the needle circumference to minimize the destruction of the integrity of the needle, but not in the same axial plane as each other. These lateral openings are perpendicular to the axis of the needle shaft or can be placed at a 45-degree angle toward the distal tip as desired to decrease the amount of tissue blockage upon piercing skin. The needle gauge may be varied depending on the desired tissue depth and particular situation. The dimensions described herein for the preferred embodiment use a 22 G×one-inch needle but all other needle sizes can be provided with proportionally-placed holes according to the size and gage of the needle in question.

The needle of the subject invention can be used in many situations that require injection through skin. The injection can be intramuscular, intradermal or subcuticular provided it requires a needle method. It can be used in dentistry for oral nerve blocks, for insulin injection in diabetic patients on a daily basis for blood sugar control, and for routine immunizations. The perforated distal holes can be easily applied to any presently-manufactured needle by means of a simple modification.

The needle can be of four specific designs. One is that of a regular straight shaft with perforated lateral holes according to the above description. The second variation is similar to the first except that the distal tip is closed and all fluid escapes from the lateral holes. The third design is that of a tapered needle (0.9 mm proximal to 0.3 mm distal) with lateral holes and an open distal tip. The fourth design is a tapered needle with lateral holes and a closed distal tip.

While the above description contains many specifics, these should not be construed as limitations of the scope of the invention, but rather as an exemplification of one preferred embodiment thereof. Many other variations are possible. For example, the distal opening can be sealed leaving the lateral holes as the only path along which the injected solution can escape or the lateral holes can be made in different sizes ranging from larger to smaller and vice versa or at a different spacing.

Accordingly, the scope of the invention should be determined not by the embodiment(s) illustrated, but by the appended claims and their legal equivalents.

It-is the object of the present invention to provide an improved hypodermic needle for use with conventional syringes that reduces or eliminates pain by decreasing the injection pressure thereby reducing fluid distension and thus pain.

In accordance with these and other drawings that will be apparent hereinafter, the instant invention will now be described with particular reference to the accompanying drawings.

BRIEF DESCRIPTION OF THE SEVERAL VIEWS OF THE DRAWINGS

FIG. 2A shows a fragmentary (distal third) side view of a needle tip in accordance with the present invention showing the first laterally-perforated hole.

FIG. 2B shows a counter clockwise 90-degree rotated view of a hypodermic needle constructed in accordance with the embodiment of FIG. 1 with the needle rotated 90 degrees about the axis of the shaft showing the second laterally-perforated hole.

FIG. 2C shows a counter clockwise 90-degree rotation relative to FIG. 2B with the third lateral hole revealed.

FIG. 2D shows a counter clockwise 90-degree rotation relative to FIG. 2C with the fourth and final hole shown.

Figure 1:
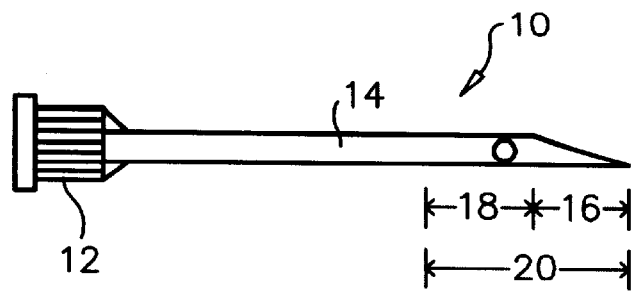
FIG. 1 shows a complete view of the present invention. Hub 12 is polypropylene and needle cannula 14 is stainless steel.

In the drawings, preferred dimensions for a 1.00 inch long needle are indicated by the following letters: dimension A is 0.0313 inch, dimension B is 0.02 inch, dimension C is 0.016 inch, dimension D is 0.025 inch, dimension E is 0.230 inch, dimension F is 0.0616 inch and dimension G is 0.351 inch.

DETAILED DESCRIPTION OF THE INVENTION

Referring now to the drawings and particularly to FIG. 1 (22 G×1 inch), the improved and newly designed hypodermic needle is shown generally at 10. Hypodermic needle 10 is comprised of hub 12, hollow, elongated, rigid shaft 14, with multitude of holes in region 18 (the last one third of the needle, approximately 0.230 inch total) near sharpened tip end 16. Needle 10 has a precisely honed edges with distal hole tip opening 16 having a size in the range of 26 G to 18 G depending on the application.

Figure 2A:
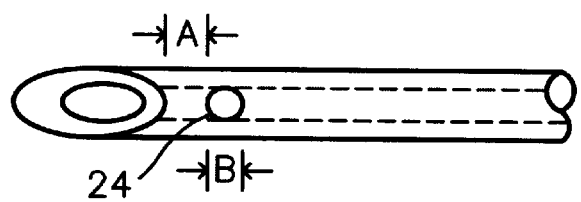
FIGS. 2A through 2D show a 22 G×1-inch regular-wall needle with 0.0313-inch-separated lateral holes in fragmented views with a total length of lateral perforations of 0.0230 inches (23 percent), when measured from the distal tip.
Figure 2B:
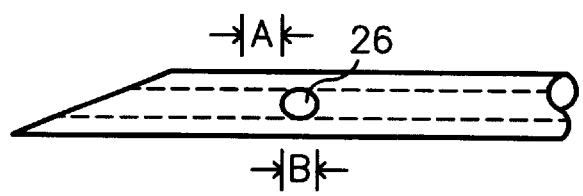
Figure 2C:
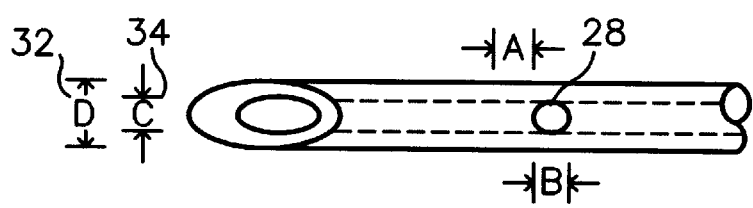
Figure 2D:
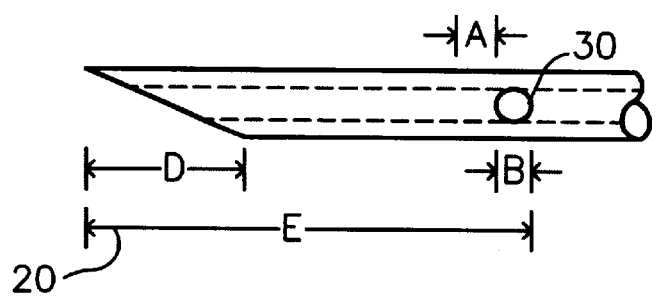
Figure 3A:
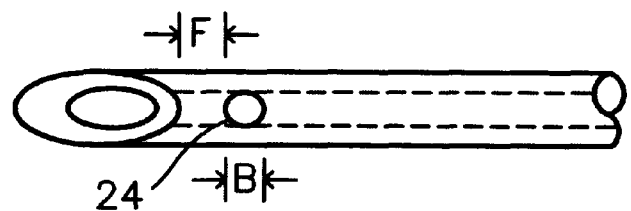
FIGS. 3A through 3D show a 22 G×1 inch regular-wall needle with 0.0616-inch separated lateral holes with a total length of the distal perforated lateral perforations of 0.351 inches from the needle tip, about 35 percent at the distal end of the needle of the present invention.
Figure 3B:
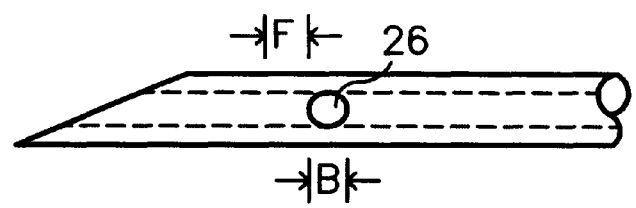
Figure 3C:
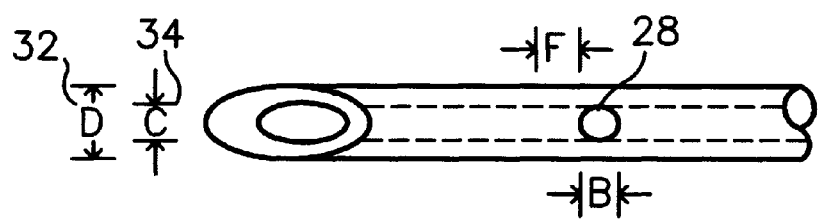
Figure 3D:
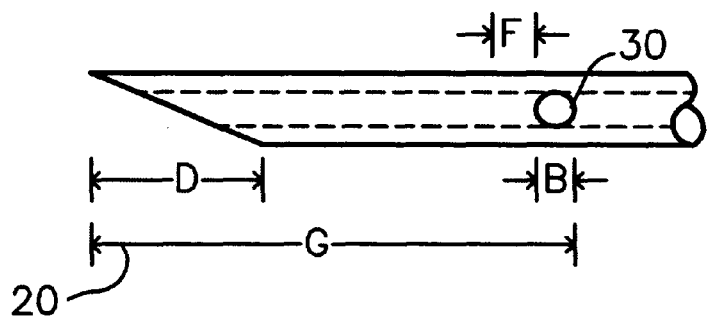

FIGS. 2A through 2D show distal one third (0.230 inch) 20 of needle 10 (1.00 inch). FIG. 2A shows a design with first lateral perforation 24 measuring 0.020 inch in diameter appearing at 0.0313 inch from beveled edge 16. The positions of perforated lateral holes 24, 26, 28 and 30 (0.02 inch) are such that they are staggered and will not lie on the same axis therefore minimizing the weakening of the structural integrity of needle 10. Holes 24–30 allow for an even distribution of injected fluids within the distal tip and keep distension of the regional tissue to a mere minimal fraction. With the decreasing distension of the surrounding tissue, pain receptors are less activated and therefore the patient will have less or no pain sensation. FIG. 2B shows second perforated hole 26 (0.02 inch diameter) design that is 0.0313 inch from hole 24 with needle 10 rotated 90 degrees counterclockwise in relation to FIG. 2A. FIG. 2C shows needle 10 rotated counterclockwise 90 degrees relative to FIG. 2B. with lateral perforated hole 28 being 0.0313 distance from lateral hole 26. Also shown are internal diameter (I.D.) 34 of needle 10, measuring 0.016 inch and outside diameter (O.D.) 32, measuring 0.025 inch. FIG. 2D shows a final rotation of needle 10 rotated 90 degrees counterclockwise relative to FIG. 2C revealing fourth distal perforated hole 30 (0.02 inch), located at a 0.0313 inch distance from perforated hole 28. Needle tip 16 can also be modified to make the opening smaller or larger to further evenly distribute the injected materials as needed with further experiments yielding other modifications. FIGS. 3A through 3D describe needle 10 with laterally-perforated holes but with a greater perforated hole separation of 0.0616 inch (35 percent) of the needle distally from hub 12.

The invention shown and described herein is considered to be a modification to an "old" invention with a more practical nature. The above changes are subtle but their impact on sensation is of great value. The company that mass produces the invention will not have to undergo a major modification in their production line to have a new and improved hypodermic injection needle that will subjectively and psychologically help patients with decreasing their fear of needles. The needle will be further modified to greatly reduce the sensation of pain once more research is underway, but the general concept is at hand to reduce pain sensation by modification of a mechanical aspect producing pain. It is recognized, however, that departures may be made therefrom within the scope of the invention, and that obvious modifications will occur to a person skilled in the art.

Experimental Observations

Simple experiments were conducted in simulated hypodermal skin samples made from concentrated, clear Jell-O®. Under direct visual observation, the Jell-O® was penetrated to a specific depth and injected with one cubic centimeter (cc) of colored dye to simulate the injection process. Two injection samples were taken from each beaker of Jell-O® to compare the effect of injections on simulated tissues. The experimental goal was to observe the functionality of the new needle with regard to tissue distension and to determine the best spacing of lateral perforations in the last 23 percent (0.23) vs. 35 percent (0.351) of the needle length.

To summarize the results and conclusion, it was observed that the new perforated needle demonstrated a more diffuse but yet localized injection with a decrease in pressure in the surrounding tissue and a decrease in the activation of sensitive nerve fibers that causes pain. Using the improved needle, in accordance with the present invention, the injected dye was delivered to a specific area with a decrease in injection pressure, thus decreasing nerve activation and the sensation of pain. Use of 0.0313 lateral perforation spacing intervals appeared to have the best localizing effect without increasing the pressure. The 0.0313 intervals maximized the concentration of the injected fluid delivered to a certain location and minimized the distension effect of the injected fluid.

What is claimed is:

1. A needle for injecting a medication through the skin, said needle comprising:

a hub; and an essentially straight shaft having a first end connected to said hub, said shaft comprising a plurality of non-overlapping longitudinal segments and having a longitudinal axis from which four radial planes extend at about ninety-degree intervals, a bore there through that is disposed along said longitudinal axis, and a sharpened end having a single, axially-oriented exit port that has a central point situated on said longitudinal axis, a longer diameter and a shorter diameter and that is in fluid communication with said bore, the length of said shorter diameter being approximately equal to the internal diameter of said bore;

wherein said shaft is provided with a plurality of lateral ports that are elliptical in cross section and located adjacent to said sharpened end, each of which ports has a width and a height that is smaller than said width and that is approximately the same as the internal diameter of said bore, is in fluid communication with said bore and is located in a different longitudinal segment and has a center that is located in a different radial plane; and wherein the center of one of said elliptical lateral ports lies in the same radial plane as the longer diameter of the exit port.

2. The needle of claim 1 wherein said lateral ports have centerlines that intersect the longitudinal axis at points and that are approximately equidistant from one another.

3. The needle of claim 2 wherein said centerlines are approximately perpendicular to said longitudinal axis.

4. The needle of claim 2 wherein said centerlines are oblique to said longitudinal axis.

5. The needle of claim 1 in combination with a syringe.

6. The needle of claim 1 wherein said hub is translucent.

7. The needle of claim 1 wherein said shaft is tapered.

8. A needle for injecting a medication through the skin, said needle comprising:

a hub; and an essentially straight shaft having a first end connected to said hub, said shaft comprising a plurality of spaced and non-overlapping longitudinal segments and having a longitudinal axis from which a plurality of radial planes extend, a bore through said shaft that is disposed along said longitudinal axis, and a second, beveled end having an exit port that has a central point situated along said longitudinal axis, and that is in fluid communication with said bore;

wherein said shaft is provided with a plurality of regularly arranged lateral ports that are located adjacent to said sharpened end, each of which ports has a width and a height that is approximately the same as the internal diameter of said bore, is in fluid communication with said bore and is located in a different longitudinal segment and has a centerline that is located in a different radial plane.

9. The needle of claim 8 wherein the lateral ports are circular in cross section.

10. The needle of claim 8 wherein four lateral ports are provided.

11. The needle of claim 8 wherein the lateral ports are spaced at approximately 0.0313 inch intervals and are all located within about 0.230 inches of the tip of the sharpened end.

12. The needle of claim 8 wherein the lateral ports are spaced at approximately 0.0616 inch intervals and are all located within about 0.351 inches of the tip of the sharpened end.

13. The needle of claim 8 wherein said lateral ports have centerlines that intersect the longitudinal axis at points and that are approximately equidistant from one another.

14. The needle of claim 13 wherein said centerlines are approximately perpendicular to said longitudinal axis.

15. The needle of claim 14 wherein said centerlines are oblique to said longitudinal axis.

16. The needle of claim 8 in combination with a syringe.

17. The needle of claim 8 wherein said hub is translucent.

18. A needle for injecting a medication through the skin, said needle comprising:

a hub; and a shaft having a first end connected to said hub, said shaft comprising a plurality of non-overlapping longitudinal segments and having a longitudinal axis from which a plurality of radial planes extend, a bore through said shaft that is disposed along said longitudinal axis, and a second, sharpened end having an exit port at its tip that is in fluid communication with said bore;

wherein said shaft is provided with a plurality of tubular lateral ports that are located adjacent to said sharpened end, each of which ports has a width and a height that is approximately the same as the internal diameter of said bore, is in fluid communication with said bore and is located in a different longitudinal segment and has a cross section that is located in a different radial plane.

19. The needle of claim 18 wherein said lateral ports have centerlines that intersect the longitudinal axis at points and that are approximately equidistant from one another.

20. A needle comprising:

a hub; and a shaft connected to said hub that has a longitudinal axis and a bore in fluid communication with said hub, a single axially-oriented end opening and a plurality of tubular, lateral openings that are situated in different longitudinal segments along the shaft and that have centerlines that are in different radial planes emanating from the longitudinal axis of the shaft.

* * * * *